(12) United States Patent
Park et al.

(10) Patent No.: US 11,820,788 B2
(45) Date of Patent: Nov. 21, 2023

(54) METHOD FOR PRODUCING SWEETENER ALLULOSE

(71) Applicant: SAMYANG CORPORATION, Seoul (KR)

(72) Inventors: Ji Won Park, Suwon-si (KR); Sung Won Park, Yongin-si (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 178 days.

(21) Appl. No.: 16/621,350

(22) PCT Filed: Apr. 17, 2018

(86) PCT No.: PCT/KR2018/004440
§ 371 (c)(1),
(2) Date: Dec. 11, 2019

(87) PCT Pub. No.: WO2019/004579
PCT Pub. Date: Jan. 3, 2019

(65) Prior Publication Data
US 2020/0157131 A1    May 21, 2020

(30) Foreign Application Priority Data
Jun. 30, 2017  (KR) .................. 10-2017-0083907

(51) Int. Cl.
*C07H 1/06*       (2006.01)
*C07H 3/02*       (2006.01)

(52) U.S. Cl.
CPC ............ *C07H 1/06* (2013.01); *C07H 3/02* (2013.01)

(58) Field of Classification Search
CPC .... C07H 1/06; C07H 3/02; C07H 1/00; A23L 27/30; A23L 27/33
USPC ........................................................ 127/58
See application file for complete search history.

(56) References Cited

U.S. PATENT DOCUMENTS

| | | | |
|---|---|---|---|
| 2,985,589 A | 5/1961 | Broughton et al. | |
| 2010/0190225 A1 | 7/2010 | Oh et al. | |

FOREIGN PATENT DOCUMENTS

| | | | | |
|---|---|---|---|---|
| CN | 104447888 | | 3/2015 | |
| CN | 104447888 A | * | 3/2015 | |
| CN | 106520863 A | * | 3/2017 | |
| EP | 3378943 | | 9/2018 | |
| JP | 6-277099 | | 10/1994 | |
| JP | 2011-206054 | | 10/2011 | |
| KR | 10-2011-0108185 | | 10/2011 | |
| KR | 10-1318422 | | 10/2013 | |
| KR | 10-2014-0021974 | | 2/2014 | |
| KR | 10-2014-0054997 | | 5/2014 | |
| KR | 10-2014-0080282 | | 6/2014 | |
| KR | 10-2016-0062349 | | 6/2016 | |
| KR | 20160062349 A | * | 6/2016 | |
| KR | 10-1723007 | | 4/2017 | |
| KR | 10-2017-0057078 | | 5/2017 | |
| KR | 2017072849 A | * | 6/2017 | ............ A23L 27/30 |
| WO | 2011-119004 | | 9/2011 | |
| WO | 2016-064087 | | 4/2016 | |
| WO | 2016-160573 | | 10/2016 | |
| WO | WO-2017059352 A1 | * | 4/2017 | ............... A23G 3/38 |
| WO | 2017-150766 | | 9/2017 | |

OTHER PUBLICATIONS

Machine translation of KR 20160062349A originally published Jun. 2016 to Lee et al. (Year: 2016).*
Eckles, et al., When to Use High-Vacuum Distillation, May 1991, Chemical Engineering (New York), vol. 98, pp. 201-203 (Year: 1991).*
Nguyen Van Duc Long et al., Separation of D-psicose and D-fructose using simulated moving bed chromatography, 2009, J. Sep. Sci., vol. 32, pp. 1987-1995 (Year: 2009).*
Sanshin: Rising Thin Film Vacuum Evaporator [online], [capture from Jun. 30, 2016]. Retrieved from the Internet < URL: https://web.archive.org/web/20160630225836/https://www.sanshin-mfg.co.jp/english/product/recycle/ltv.html> (Year: 2016).*
Machine translation of CN 106520863 originally published Mar. 2017 to Kong et al. (Year: 2017).*
Machine translation of CN 104447888A originally published Mar. 2015 to Li et al. (Year: 2015).*
Machine translation of KR 2017072849 A originally published Jun. 2017 to An et al. (Year: 2017).*
Nguyen Van Duc Long et al., "Separation of D-psicose and D-fructose using simulated moving bed chromatography", J. Sep. Sci. vol. 32, p. 1987-1995 (2009).
KIPO., PCT Search Report & Written Opinion of PCT/KR2018/004440 dated Jul. 25, 2018.
Toma, Koichi, "Multi-effect evaporator, Mainly for sugar manufacturing factory", Faculty of Agriculture, Ryukyu University, Jun. 1968.
Toma, Koichi, "Concentration of sugar cane juice at sugar separation factory", Faculty of Agriculture, Ryukyu University, Apr. 1965.
Nguyen Van Duc Long et al. "Separation of D-psicose and D-fructose using simulated moving bed chromatography", J Sep Sci. Jun. 2009;32(11):1987-95. doi: 10.1002/jssc.200800753.
EPO, European Search Report of EP 18823847.1 dated Mar. 12, 2021.

* cited by examiner

*Primary Examiner* — Sheng H Davis
*Assistant Examiner* — Ritu S Shirali
(74) *Attorney, Agent, or Firm* — LEX IP MEISTER, PLLC

(57) ABSTRACT

The present invention relates to a method of preparing an allulose with stability at high yield, by concentrating products obtained by separating a solution containing allulose of a functional sweetener with high purity, to reduce the content of impurities such as fructose and reducing sugars and increase the content of allulose.

10 Claims, No Drawings

METHOD FOR PRODUCING SWEETENER ALLULOSE

TECHNICAL FIELD

The present invention relates to a method of preparation an allulose with stability at high yield, by concentrating an allulose-containing solution at a low temperature to reduce the content of impurities such as fructose and reducing sugars and increase the content of allulose.

BACKGROUND ART

Allulose (D-allulose) is an epimer of fructose (D-fructose) and is one kind of functional saccharides known as a rare saccharide, and it has been known to have an effect on prevention and improvement of diabetes, since it has sweetness of about 60 to 70% of sugar and almost zero calorie. In addition, allulose is known to have excellent solubility, and it is one of materials where utilization for food is attracting attention.

There are a chemical method and a biological method in the method for preparing allulose, and recently, a method for preparing allulose with a biological method performs allulose conversion reaction by contacting fructose-containing substrate solution with an allulose epimerase or a microorganism producing the enzyme. The fructose-containing solution that is a reaction raw material used in the allulose conversion process may be a fructose isomerization reaction product obtained by isomerization reaction of glucose obtained from the degradation of starch, etc.

However, it is required to separate allulose with high purity, since the reaction solution comprising D-allulose is a low purity product. In fact, various methods have been applied to separate industrially produced materials with high purity, and in case of saccharides, products are mostly produced by crystalizing after preparing a high purity solution using chromatography.

To obtain a high purity allulose product from the allulose conversion reaction product solution, a high purity separation process is performed, and in addition, to obtain allulose crystals, an allulose crystallization process may be performed using high purity allulose syrup. There is a need for a method for concentrating allulose in high yield by minimizing conversion from allulose from allulose fractions obtained from the allulose separation process into impurities and increasing the allulose content, and a method of concentration for increasing the utilization rate of raw materials, and having an allulose concentrate with storage stability for a storage period.

DISCLOSURE

Technical Problem

Accordingly, an embodiment of the present invention relates to a method for concentrating allulose from an allulose aqueous solution with high yield and high storage stability, to minimize the conversion from allulose to impurities and increasing the allulose content, and a device used therefor.

An additional purpose of the present invention relates to a method of preparing allulose comprising a method for concentrating allulose with a high yield by minimizing the conversion from allulose to impurities and increasing the allulose content, and a device used therefor.

Technical Solution

The present invention relates to a method for concentrating allulose from an allulose aqueous solution at a low temperature, to increase the allulose content and decrease the content of impurities such as fructose and reducing sugars, and to prepare the allulose with high yield and high storage stability The allulose aqueous solution may be obtained from allulose fractions obtained from the allulose separation process.

When the solid content is increased to high Brix at a time through a concentration process of allulose, there are problems that the contents of impurities such as fructose and reducing sugars or allulose conversion reaction products are increased, thereby lowering allulose purity, and the final production yield and quality of products. In addition, the storage stability is low for a storage period. Accordingly, in consideration to production yield, product quality and storage stability, other concentration methods being different from the conventional starch sugar preparation method may be needed.

Accordingly, the present invention has an advantage of increasing the utilization efficiency of raw material and the storage stability of the allulose concentrate solution, since a method for concentrating an allulose aqueous solution at a low temperature, preferably, the adoption of a method for performing a concentration process by at least 2 or more of distillation processes can minimize the conversion of allulose to impurities in the concentration process and increase the allulose content, thereby producing allulose at a high yield. The low temperature concentration process may be performed by concentrating step by step as divided into at least 2 steps or more using a thin film evaporator or a multiple effect evaporator.

The allulose concentrates obtained according to the concentration method of the allulose solution in the present invention may obtain an allulose concentrate solution having excellent storage stability in which the decreased content of the allulose is 3.5% by weight or less, 3.0% by weight or less, 2.5% by weight or less, or 1.5% by weight or less, under the storage condition at 35° C. for 5 weeks, based on 100% by weight of the allulose content before concentration.

Accordingly, it has been confirmed that the present invention can prepare products from an allulose aqueous solution at a comparatively low temperature without a content change in the concentration and decreased content of allulose, and products with uniform quality can be produced stably.

Hereinafter, the present invention will be described in more detail.

The present invention relates to a method for preparing an allulose concentrate solution having the solid content of 60 Brix or more, for example, 60 Brix or more to 85 Brix or less, in which the method comprises obtaining an allulose aqueous solution containing allulose; and distilling the allulose aqueous solution at 85° C. or less, for example, 40 to 85° C. of the concentrate solution. Herein, the term 'Brix' is defined as the mass (g) of saccharides comprised in 100 g of sample solution.

The distilling may be repeatedly performed twice or more. The distilling may be performed by at least 2 or more of distilling steps.

When the distillation step is performed by at least 2 or more of steps, each step may be performed as divided by differently setting at least one of conditions of the distilling process, in consideration of distilling temperature, distilling time, distilling method, solid content (Brix) of the concentrated solution, purity of allulose comprised in the concentrated solution, and the like.

Specifically, when the distilling process of the present invention is performed by 2 steps, they comprise a step for preparing a low concentrate solution having the total solid content of 10 Brix or more to 60 Brix or less and a step for preparing a high concentrate solution having the total solid content of more than 60 Brix to 85 Brix or less.

The lower limit value of the final solid content in the allulose concentrate solution obtained by the method of preparation according to the present invention may be more than 60 Brix or more, more than 65 Brix or more, more than 70 Brix or more, 75 Brix or more, 78 Brix or more, 79 Brix or more, 80 Brix or more, 81 Brix or more, 82 Brix or more, 83 Brix or less, or 84 Brix or more, and the upper limit value of the final solid content may be 85 Brix or less, 84 Brix or less, 82 Brix or less, 81 Brix or less, 80 Brix or less, 79 Brix or less, 78 Brix or less, 75 Brix or less or 70 Brix or less. In addition, the final solid content of the allulose concentrate solution may be in a range of combining one selected from the lower limit value and one numerical value selected from the upper limit value, and for example, it may be 60 Brix or more to 80 Brix, more than 60 Brix to 80 Brix, 65 to 85 Brix, 65 to 80 Brix, or 68 to 85 Brix, or the like.

In addition, the concentration may performed by a concentration process divided into at least 2 steps of primarily concentrating from the initial total solid content (Brix) 5 to 15 Brix to 10 Brix or more to 60 Brix or less, for example, to 10 to 55 Brix, 10 to 60 Brix, 15 to 55 Brix, 15 to 60 Brix, 10 to 19 Brix, 20 to 29 Brix, 30 to 39 Brix, 40 to 49 Brix or 50 to 60 Brix or less, and secondarily concentrating the primary concentrated solution to more than 60 Brix to 85 Brix or less, for example, more than 60 Brix to 80 Brix, 65 to 85 Brix, 65 to 80 Brix, or 68 to 85 Brix, and thus, the content of allulose may be stably maintained after the high purity separation.

The temperature difference between the solution in the step for preparing a high concentrated solution and the solution in the step for preparing a low concentrated solution may be 0° C. to 35° C., for example, 0° C. to 25° C., 5 to 25° C., 10 to 25° C., 5° C. to 35° C., 10° C. to 35° C., 0° C. to 20° C., 5° C. to 20° C., or 10° C. to 20° C.

For example, the distillation concentration process may be performed in a range of the temperature of the allulose solution of 40° C. to 85° C. When the concentration process is performed by 2 steps, the solution temperature of primary concentration is 40° C. to 75° C., and the solution temperature of secondary concentration is 50° C. to 85° C.

As a specific embodiment, the two-step concentration process using a multiple effect evaporator may include a first step of concentrating at the temperature of the allulose solution of 40° C. to 60° C. to obtain the concentrate product having 20 to 29 Brix, and then a second step of concentrating at a solution temperature of 60° C. to 85° C., or a first step of concentrating at the temperature of the allulose solution of 45° C. to 70° C. to obtain the concentrate product having 30 to 39 Brix, and then a second step of concentrating at a solution temperature of 50° C. to 75° C.

In addition, the two-step concentration process using a thin film evaporator may include a first step of concentrating at the temperature of the allulose solution of 40° C. to 55° C. to obtain the concentrate product having 10 to 60 Brix, and then a second step of concentrating at a solution temperature of 45° C. to 75° C.

The pressure condition (inside the distiller) in the distilling according to the present invention is preferably 100 mmHg or less (for example, 0.0001~10 mmHg, more specifically, 0.0001~8 mmHg), and is more preferably 5 mmHg or less (for example, 0.001~5 mmHg), and is much more preferably 1 mmHg or less (for example, 0.01~1 mmHg, more specifically, 0.01~0.8 mmHg). To achieve such a pressure condition, a decompression pump may be used. In the distilling, it may be out of the decompression condition, or for example, by further including a step of stopping the decompression pump between the step of for preparing a low concentrated solution and the step for preparing a high concentrated solution, or for example, it may be performed by transferring from a concentration device for preparing a low concentrated solution to a concentration device for preparing a high concentrated solution.

When the distillation pressure is higher than 10 mmHg, it is necessary to raise the distillation temperature to distill anhydrous sugar alcohol, thereby causing the described problems. On the other hand, the cost of the high vacuum device is needed additionally to lower the distillation pressure, and thus excessively low distillation pressure is not preferable. According to a preferable embodiment of the present invention, when performing the distilling, it may be further decompressed through a distillation residue discharge line, in addition to decompression in the inside the distiller through a vacuum line The allulose aqueous solution for preparing a concentrated solution according to the present invention may be a high purity allulose solution comprising allulose at a content of 90% by weight or higher, for example, 95% by weight or higher. The viscosity of the allulose aqueous solution may be 2 cps to 40 cps at the temperature of 45° C., and the electrical conductivity may be 0.01 to 100 uS/cm, 0.1 to 100 uS/cm, preferably, 0.01 to 30 uS/cm, or 0.1 to 30 uS/cm.

An example of the allulose aqueous solution which is subjected to the concentration process may be allulose fractions obtained by performing a simulated moving bed (SMB) chromatography separation process using column chromatograph in which a calcium activator-attached cation exchange resin is packed, and specifically, it may be allulose fractions obtained by obtaining allulose conversion reaction products from fructose-containing raw materials using a biological catalyst, and performing activated carbon treatment, ion purification and simulated moving bed (SMB) chromatography separation processes of the allulose conversion reaction products. The allulose fractions may be themselves obtained from the SMB chromatograph separation process or be obtained through the ion purification process. The fructose content of the fructose-containing raw material may be 85% by weight or higher, based on 100% by weight of the total solid content of the allulose conversion reaction, and it may use a biological catalyst having an allulose conversion rate of 15% to 70% in the allulose conversion reaction. The allulose aqueous solution will be described in more detail below.

The allulose concentrate solution obtained according to the concentration method of the present invention may have a solid content of 60 or more to 85 Brix or less, for example, more than 60 Brix to 80 Brix, 65 to 85 Brix, 65 to 80 Brix, or 68 to 85 Brix. The allulose concentrate solution may have allulose purity of 90 wt/wt % or more, for example, 91 wt/wt % or more, 92 wt/wt % or more, 93 wt/wt % or more, 94 wt/wt % or more, 95.5 wt/wt % or more, 96% by weight or higher, 97% by weight or higher, 98% by weight or higher, or 99% by weight. The allulose content comprised in the allulose concentrates has little variation with the allulose content of the allulose fractions obtained from the SMB chromatography separation process, and the solid content is increased to allow for a subsequent crystallization process.

Herein, 'reducing sugar' means a sugar which has a free aldehyde group or ketone group and exhibits reducibility. The reducing sugar of the present invention includes free monosaccharides except for allulose, glucose and fructose, and sugar-alcohols obtained by reducing aldose or ketose. More specifically, the kinds of the reducing sugar of the present invention include monosaccharides comprising arabinose, xylose, mannose, altrose and allose; and sugar-alcohols comprising glucitol, mannitol, altritol and allitol.

The total content of the fructose and reducing sugars comprised in the allulose concentrates may be 4.5% by weight or less, preferably, 4.0% by weight or less, 3.7% by weight or less, 3.5% by weight or less, 3.0% by weight or less, 2.0% by weight or less, or 1.0% by weight or less. The allulose concentrate solution may have the fructose content of 3.0% by weight or less, and the content of reducing sugars of 2.5% by weight or less, and preferably, the total content of the fructose and reducing sugars satisfies the condition of 4.5% by weight or less. As a specific example, the allulose concentrate solution may has the fructose content of 2.8% by weight or less, and the content of reducing sugars of 2.0% by weight or less, 2.0% by weight or less, 1.5% by weight or less, 1.3% by weight or less, 1.0% by weight or less, or 0.5% by weight or less.

The method for obtaining an allulose concentrate solution according to the present invention may be performed at which a temperature of the high-purity allulose solution is 85° C. or less, for example, 40° C. to 85° C., and specifically, it may be performed using a thin film evaporator or multiple effect evaporator.

The thin film evaporator which can be used in the preparation method of allulose in the present invention includes an internal or external thin film evaporator. A specific example of the internal thin film evaporator is a condenser-embedded thin film evaporator, and it equips an internal condenser, a raw material input line, a distillation residue discharge line, a side branch line for vacuum formation, a vacuum line and a distillate discharge line, and in addition, it comprises a heating jacket for heating, a wiper, a condenser guard, and a coolant inflow/outflow line. The condenser-embedded thin film evaporator which can be used in the present invention may further comprise additional components in addition to the above components if necessary, and its shape may vary.

The multiple effect evaporator which can be used in the method of preparation of allulose of the present invention enhances the energy efficiency by the method of using vapor evaporated from the solution inputted by vapor supplied as a heat source as heat source vapor of the next effect concentrator (evaporator). As the evaporator is connected as various effects, evaporation occurs sequentially, and the solution inputted initially is concentrated at a high concentration. A representative method for enhancing the evaporation performance of the multiple effect evaporation system includes flash evaporation, vapor recompression, vapor bleeding, and the like. The flash evaporation is a phenomenon which a high temperature and high pressure of liquid is decompressed in a flash tank and evaporation occurs in a moment, and it is separated into liquid and gas phases. The vapor produced at that time has high energy and is inputted into an evaporation system, and thereby it increases overall energy efficiency. The vapor separation means increasing the temperature of the solution by vapor separated from the evaporation system. A representative device for increasing the temperature of the solution is a preheater, and it increase the temperature of the solution using vapor separated from the evaporator as an energy source. When the temperature of the solution inputted into the evaporator is increased, the difference of temperatures becomes larger, and therefore the amount of moisture evaporated from the solution is increased. The vapor recompression means compressing low pressure vapor produced during the evaporation process by a high pressure to resupply high temperature vapor into the evaporation system. High energy vapor is inputted into the evaporation system due to the increase of the inputted vapor flow rate and increase of the temperature, and the evaporation performance is improved. The vapor is condensed by heat exchange with the solution when the vapor is inflowed into the evaporator, and the solution absorbs a discharged condensation heat, and passes through an evaporation process, and thereby it is separated into vapor and a concentrated solution. The separated vapor is used as an energy source of the next evaporator and the concentrated solution is concentrated at a high concentration through the evaporation process. By such a chain reaction, evaporation occurs and the concentration of the solution is increased.

It means a method that to collect and use latent heat of vapor, commonly 2 to 7 of the same type of evaporators are connected in series, and evaporation is conducted by sequentially supplying the vapor used in the initial tube to a next tube sequentially, and using it as a heat source. It is for cooling the vapor produced in the final tube with a condenser, and exhausting with a vacuum pump, and making it the lowest pressure, and gradually decreasing the pressure and boiling point of each tube to make heating effective to increase the energy efficiency, and it is used for concentration of liquid components. Preferably, it may be a decompression evaporator.

A triple effect evaporator of a triple effect (effect number N=3) of evaporator is a system consisting of a first effect evaporator, a second effect evaporator, a third effect evaporator, a condenser, a condensed water pump and a vacuum pump, and the like, as major instruments, in addition to a water ring vapor compressor, and if necessary, it may further comprise additional components in addition to the above components, and its shape may vary.

Another embodiment of the present invention relates to a method of preparation of allulose comprising the method for preparing allulose concentrates.

As a specific embodiment, the method of preparation of allulose of the present invention may comprise (1) an allulose conversion process for preparing an allulose conversion reaction product by performing a biological conversion reaction of allulose with a fructose-containing raw material; (2) an allulose separation process for obtaining allulose fractions and fructose raffinates by performing primary ion purification and separation using simulated moving bed (SMB) chromatography of the conversion reaction product; and (3) a process for concentrating the allulose fractions, and additionally, it may comprise (4) a process for obtaining allulose crystals using the allulose concentrates.

The allulose preparation method of the present invention may use both continuous and batch modes, and preferably, it is a continuous process. In one embodiment of the present invention, the product obtained in the allulose conversion process is a mixture comprising fructose that is a raw material substrate and allulose that is a product, and allulose fractions which has the increased content of allulose that is a targeted material through the high purity separation process and the residual solution are obtained, and in the residual solution, fructose that is the substrate of the allulose conversion reaction is comprised in quantity, and therefore it may mean an excessive amount of raffinates. Herein, the term "raffinate" is also called residual solution, and the product obtained as the inputted raw material passes through the separation process includes targeted fractions comprising targeted materials to increase the content by the separation process, and a residual solution comprising materials to eliminate or reduce the content in the separation process, or the like, and it is called a residual solution raffinate.

The allulose fractions obtained in the high purity separation process using SMB chromatography in the allulose preparation process of the present invention may be commercialized as liquid syrup by passing through an allulose concentration process, or be commercialized as allulose crystals by passing through an allulose crystallization process. It is a step for preparing concentrates obtained by ion purification and concentration of the allulose fractions obtained in the SMB chromatograph separation process. The concentrates may be used as an allulose syrup product, or may be inputted into a crystallization process and be prepared as allulose crystals.

Hereinafter, an allulose preparation process using the process for concentrating allulose fractions obtained in the high-purity separation process of the allulose conversion reaction product according to the present invention will be described by step in detail.

An allulose conversion process is a process for converting from a fructose-containing raw material into allulose by performing the allulose conversion reaction, resulting in obtainment of a reaction solution containing allulose converted from fructose as the product of the process.

In one specific embodiment of the present invention, the allulose according to a biological method may be produced by culturing a strain producing an allulose epimerase or a recombinant strain being included a gene encoding the allulose epimerase and reacting the allulose epimerase obtained therefrom with a fructose-containing raw material. The allulose epimerase may be used by a liquid reaction or a solid reaction using an immobilized enzyme.

In addition, it may be prepared by obtaining a strain producing an allulose epimerase or a recombinant strain being included a gene encoding the allulose epimerase, and reacting a composition for producing allulose comprising one or more kinds selected from the group consisting of a microbial cell of the strain, culture of the strain, lysate of the strain and extract of the lysate or culture, with a fructose-containing raw material. When the allulose is prepared using the microbial cell of the strain producing the allulose epimerase, it may be performed by a liquid reaction or a solid reaction using an immobilized microbial cell.

The allulose conversion process according to one embodiment of the present invention is performed by a biological method, and the step of immobilizing the allulose epimerase in a carrier may further comprise a step of packing an immobilized enzyme into a column and a step of supplying a fructose solution into the packed column. The column in which a carrier in which an enzyme or a microbial cell is immobilized is to be packed and the method for packing into the column may by performed by selecting a suitable one according to the used enzyme or microbial cell, or immobilized carrier by those skilled in the art. In one specific embodiment of the present invention, a packed-bed column may be prepared by packing the immobilized enzyme. By supplying a fructose solution that is a substrate into a packed column, an enzyme reaction that is conversion of fructose into allulose may be conducted.

The detailed technical contents regarding allulose and its preparation method are disclosed in Korean patent publication No. 2014-0021974, Korean patent publication No. 2014-0054997, Korean patent publication No. 2014-0080282, or Korean patent No. 10-1318422.

The fructose raw material put into the allulose conversion process according to the present invention may be prepared by a biological method or chemical method, preferably by a biological method. The fructose as a raw material may be provided as a liquid phase raw material, or a powdery raw material such as fructose powder, and in case of fructose syrup, it may be the product obtained in the biological method or chemical preparation method, or one prepared by dissolving fructose powder in a solvent such as water.

In an embodiment of preparing the fructose raw material with a biological method, the fructose may be obtained by performing a fructose isomerization process which isomerizes a glucose-containing raw material with a fructose isomerase or a microbial cell producing the enzyme and passing through a process for separation, purification and concentration of the fructose.

In the method for producing allulose, for effective production of allulose, the concentration of fructose used as a substrate may be 85 w/v % or more, 90 w/v % or more, or 95 w/v % or more, for example, 85 to 99 w/v %, 88 to 99 w/v %, 88 to 99 w/v %, 85 to 87% (w/v), 88 to 90% (w/v), 91 to 93% (w/v), 94 to 99% (w/v) or 97 to 99% (w/v), based on the total reaction products. The concentration of fructose may be decided by considering economics of process and solubility of fructose, and the fructose may be used as a solution prepared by dissolving fructose in a buffer solution or water (for example, distilled water).

In one embodiment of the present invention, the fructose raffinate obtained from the high purity separation process of allulose preparation may be inputted alone as a raw material of the allulose conversation reaction of allulose preparation, or together as a novel fructose raw material. When a mixture of the fructose raffinate and novel fructose raw material is used as a reaction raw material of the allulose conversion reaction, to maximize the utilization of the fructose raffinate and maintain the yield of allulose obtained in the conventional process at a maximum, the mixing ratio of the fructose raffinate and novel fructose raw material may be appropriately adjusted.

As the separation process of the allulose conversion reaction product according to the present invention, the allulose preparation process according to the present invention may perform a separation process of the allulose conversion reaction product comprising ion purification and simulated moving bed (SMB) chromatograph separation processes of the allulose conversion reaction product. In one specific embodiment, the allulose conversion reaction product may be separated into allulose fractions which have higher allulose content than the conversion reaction product, and fructose raffinates, by performing SMB chromatography separation, and the allulose fractions may be inputted into an allulose concentration process or a crystallization process. It may comprise separation/purification so that the allulose content in the allulose fractions is 85% by weight or higher, for example, 85% by weight to 95% (w/w) or more.

The ion purification process in the allulose preparation process is a process for removing ion comprised in reactants, and it may be conducted before and/or after SMB chromatography separation process. The primary ion purification which performs ion purification process before conducting the SMB chromatography separation may be carried out by the same or different method with the following secondary ion purification of allulose fractions, and for example, it may be performed by using 1 or 2 or more separation columns packed with same kind or different kinds of ion exchange resin. The ion purification process may be performed at 35 to 50° C. temperature, for example, 38 to 58° C., considering physical properties of resin used for ion purification and ion purification efficiency.

In one embodiment of the present invention, before performing the primary ion purification process of the allulose conversion reaction product, selectively, a process for treating the allulose conversion reaction product with an activated carbon may be further performed.

In one embodiment of the present invention, the high purity separation step using SMB chromatography is a separation method useful for securing stability of materials, due to no phase change in the separation process. Among them, a chromatography separation method has been used in abundance as a liquid phase adsorption separation method. Among them, a simulated moving bed (SMB) adsorption separation method is a separation technology proposed in U.S. Pat. No. 2,985,589 in 1961, and has an advantage that the purity and productivity are excellent and the use of less solvent is possible, compared to the conventional batch chromatography, by continuous separation using many of columns. The simulated moving bed (SMB) adsorption separation process is a process, in which injection of separation target mixture and production of raffinate and extract are implemented continuously.

Since a cation exchange resin of strong acid in which a salt is added, which is widely used for a process of monosaccharide separation is used as a separation resin in the SMB, metal ions are comprised in products obtained after performing the separation process. An example of cation exchange resin of strong acid may be a cation exchange resin in which a calcium activated group is attached.

The high purity separation process may be performed at a temperature of 45 to 70° C., for example, 50 to 65° C.

The preparation process of the allulose concentrate is as described above.

As a step for crystallization of the allulose concentrates according to the present invention, in one specific embodiment of the present invention, the method for preparing allulose crystals may comprise a step of the secondary ion purification of allulose fractions obtained in the SMB chromatography separation process, a step of concentrating the ion purified allulose fractions, and a step of crystallizing allulose from the concentrates to obtain allulose crystals and allulose crystallization mother liquor, and selectively, may further comprise a recovering process, a washing process and a drying process of allulose crystals.

The specific embodiment of preparation of allulose crystals may comprise the primary ion purification, SMB chromatography separation, the secondary ion purification, concentration and crystallization processes, and selectively, may perform an activated treatment process, an ion purification process, or both activated treatment process and ion purification process to the allulose conversion reaction product.

The method for preparing allulose crystals according to the present invention may implement crystallization by regulating temperature and concentration of allulose concentrate solution, and specifically the supersaturated state may be maintained by declining the temperature of allulose solution or changing the concentration of D-allulose in D-allulose solution. In one specific embodiment of the present invention, the crystallization progress may be monitored by observing samples taken at regular intervals in the crystallization step with naked eyes or a microscope or analyzing the sugar concentration in supernatant collected from centrifugation of samples, and according to the result, the temperature or concentration of D-allulose may be controlled. When the allulose concentrate solution is cooled and crystallized to prepare allulose crystals, the crystal growth may be induced by repeatedly conducting temperature rising and cooling, after rapidly cooling in the temperature range of 10 to 25° C. through a heat exchanger.

The method for preparing allulose crystals according to the present invention may further comprise various solid-liquid separations, for example, a step of recovering by centrifugation, a step of washing with deionized water, and a step of drying. The drying step may be performed in a fluidized bed drier or vacuum drier, but not limited thereto. The allulose comprised in the allulose crystals may be 94% by weight or higher, 95% by weight or higher, 96% by weight or higher, 97% by weight or higher, 98% by weight or higher, or 99% by weight or higher, based on 100% by weight of the total solid content.

The allulose crystallization mother liquor according to the present invention may be filtrate obtained after removing allulose crystals in the crystallization process, and in addition, may further comprise washing water obtained in the crystal washing step. The allulose crystallization mother liquor may have the allulose content of 80% by weight or higher, for example, 80% by weight to 99% by weight or 85% by weight to 96% by weight, based on 100% by weight of the total solid content, and the solid content may be less than 70 Brix, for example, 60 Brix or more to lower than 70 Brix.

As a recycle process of the allulose crystallization mother liquor according to the present invention, the allulose crystallization mother liquor obtained in the crystallization step may be utilized by being put into the separation process of allulose conversion reaction product. Specifically, the allulose crystallization mother liquor may be recycled for preparation of allulose by being put into one or more separation processes selected from the group consisting of activated carbon treatment, ion purification and simulated moving bed (SMB) chromatography separation processes.

Specifically, an example of the separation process, may perform the primary ion purification process and SMB chromatography separation process to allulose conversion reaction product, or perform activated carbon treatment, ion purification and simulated moving bed (SMB) chromatography separation process to allulose conversion reaction product, and before performing the SMB chromatography separation process in the separation process, selectively, may further perform a concentration process. The separation process is same as described in the item of the separation process of allulose conversion reaction product.

In one embodiment, when the allulose crystallization mother liquor is put into the primary ion purification process and ion purification process is performed with allulose conversion reaction product, it may be treated with ion purification and SMB chromatography separation processes, or treated with activated carbon treatment process, ion purification and SMB chromatography separation process in order. In addition, selectively, a concentration process may be further performed before the SMB chromatography separation process.

Advantageous Effects

The method of preparation of an allulose concentrate solution according to the present invention is particularly a method for performing a concentration process under a low temperature condition, thereby preventing quality degradation of allulose products and improving the allulose purity and yield and increasing the availability of raw materials and enhancing the storage stability of allulose.

DETAILED DESCRIPTION OF THE EMBODIMENTS

Hereinafter, the present invention will be described in more detail by following examples. However, these examples are intended to illustrate the present invention only, but the scope of the present invention is not limited by these examples.

Preparative Example 1. Preparation of Allulose Syrup

An allulose syrup was prepared from a fructose substrate by the biological method substantially same with the preparation method disclosed in the Korean laid-open patent publication No. 2014-0054997.

Specifically, the encoding gene of allulose epimerase derived from *Clostridiuim scindens* (*Clostridiuim scindens* ATCC 35704) (DPE gene; Gene bank: EDS06411.1) was introduced into a recombinant vector (pCES_sodCDPE), and *Corynebacterium glutaricum* was transformed by using the prepared recombinant vector (pCES_sodCDPE) plasmid with electroporation. A bead including the transformed *Corynebacterium glutaricum* cell was prepared and packed into an immobilization reaction column, and an allulose syrup was prepared from 40 Brix of 88% by weight of fructose or 95% by weight of fructose. That is, the allulose syrup of 21~23 (w/w) % of which solid mixture weight ratio of glucose:fructose:allulose:oligosaccharide is 41:39:15:5 from 88% by weight of fructose-containing substrate (allulose syrup A), and the allulose syrup of 24~27 (w/w) % of which glucose:fructose:allulose:oligosaccharide=6:67:25:2 from the raw material comprising 95% by weight of fructose content (allulose syrup B).

Comparative Example 1

To produce 10 tons of solids of 95% by weight of allulose content by using the fructose-containing raw material solution of 88% by weight or 95% by weight of fructose content obtained in Preparative Example 1, the allulose conversion process and separation process were carried out at flow rate 3.8 m³/hr.

Specifically, the allulose content of the allulose syrup obtained through the allulose conversion process of the raw material substrate solution (allulose syrup) of 88% by weight or 95% by weight of the fructose content was 20 to 27% by weight, and the syrup having an allulose concentration of 45 to 55% by weight was obtained after performing ion purification and concentration processes. Allulose fractions of 5 to 15% by weight were obtained by performing high purity chromatography using $Ca^{2+}$ type separation resin.

The allulose fractions were put into the ion purification process and were concentrated using a multiple effect evaporator after setting the electrical conductivity to 20 uS/cm or less. The concentration was conducted by 10 m³/hr per hour, and the temperature of steam was 125° C. to 140° C. Then, the concentration was conducted as the temperature of the solution was 86° C. to 100° C. The corresponding steam temperature condition was a concentration temperature commonly used in the starch sugar industry. The concentration was performed at a time from initially 5 to 15% by weight to 70 to 72% by weight based on the allulose content, and the time taken to concentrate the allulose fractions in multiple effect equipment was 8 minutes to 15 minutes. The concentrated product was cooled by 10 to 30° C. temperature through a heat exchanger and was packaged in a PE container. For contents by each process, the result of the concentration process of allulose syrup A was shown in Table 1, and the result of the concentration process of allulose syrup B was shown in Table 2. In the following Table 1 and Table 2, the contents of allulose, glucose, fructose and reducing sugar were measured using HPLC.

As Table 1 and Table 2, it was shown that the allulose content of the high purity allulose was reduced in the concentration process.

TABLE 1

| Classification | Brix | Saccharides including disaccharides or higher degree of polymerization | Glucose | Fructose | allulose | Reducing sugar |
|---|---|---|---|---|---|---|
| Fructose raw material | 50 | 1.1% | 5.0% | 88.1% | 0.0% | 5.8% |
| Conversion reaction product | 50 | 1.1% | 5.0% | 65.2% | 22.9% | 5.8% |
| Allulose fraction after high purity separation | 5~9 | 0.0% | 0.0% | 1.8% | 97.2% | 1.0% |
| After ion purification | 5~9 | 0.0% | 0.0% | 1.8% | 97.2% | 1.0% |
| After concentration | 70.5 | 0.0% | 0.4% | 3.4% | 94.5% | 1.7% |
| Final container | 70.5 | 0.0% | 0.4% | 3.4% | 94.5% | 1.7% |

TABLE 2

| Classification | Brix | Saccharides including disaccharides or higher degree of polymerization | Glucose | Fructose | allulose | Reducing sugar |
|---|---|---|---|---|---|---|
| Fructose raw material | 50 | 0.1% | 3.5% | 95.2% | 0.0% | 1.2% |
| Conversion reaction product | 50 | 0.1% | 3.5% | 68.1% | 27.1% | 1.2% |
| Allulose fraction after high purity separation | 10~15 | 0.0% | 0.0% | 1.5% | 97.6% | 0.9% |
| After ion purification | 10~15 | 0.0% | 0.0% | 1.5% | 97.6% | 0.9% |
| After concentration | 71.1 | 0.0% | 0.3% | 2.9% | 95.1% | 1.7% |
| Final container | 71.1 | 0.0% | 0.3% | 2.9% | 95.1% | 1.7% |

As shown in the Table 1 and Table 2, it was confirmed the result that the brix of allulose fractions was decreased in the high purity separation process as the fructose content of the fructose raw material was low, and thereby the allulose content when passing through the concentration process was lowered. When the solid content is increased by 70% by weight at a time through the present concentration process, in consideration to production yield and product quality, to maintain the allulose production yield, other concentration methods different from the conventional starch sugar preparation method may be needed.

Example 1

As Comparative example 1, (allulose syrup A) was obtained, and the allulose conversion process and separation process were performed using it. Specifically, the allulose content of the allulose syrup obtained through the allulose conversion process of the raw material substrate solution (allulose syrup) of 88% by weight of the fructose content was 20 to 27% by weight, and the syrup having an allulose concentration of 45 to 55% by weight was obtained after performing ion purification and concentration processes. Allulose fractions of 5 to 15% by weight were obtained by performing high purity chromatography using Ca+ type separation resin.

The allulose fractions were put into the ion purification process and were concentrated by 2-step concentration using a multiple effect evaporator after setting the electrical conductivity to 20 uS/cm or less. The concentration was conducted by primary concentration from the initial solid content (brix) 5 to 15% by weight to 20 to 29% by weight, and secondary concentration to 70 to 72% by weight again.

In case of the primary concentration, the concentration was conducted, as the temperature of steam was 80° C. to 90° C., and then the temperature of the solution was increased to 45° C. to 50° C. In case of the secondary concentration, it was conducted, as the steam temperature was increased to 110° C. to 120° C. and the concentration temperature of the allulose solution was 70° C. to 80° C. The time taken in concentration of allulose fractions in multiple effect equipment was 8 minutes to 15 minutes for both the primary and secondary concentration.

The concentrated product was cooled to 10 to 30° C. temperature through a heat exchanger and was packaged in a PE container. The contents by each process were shown in the following Table 3.

TABLE 3

| Classification | Brix | Saccharides including disaccharides or higher degree of polymerization | Glucose | Fructose | allulose | Reducing sugar |
|---|---|---|---|---|---|---|
| Fructose raw material | 50 | 1.1% | 5.0% | 88.1% | 0.0% | 5.8% |
| Conversion reaction product | 50 | 1.1% | 5.0% | 65.2% | 22.9% | 5.8% |
| Allulose fraction after high purity separation | 5~8 | 0.0% | 0.1% | 1.7% | 97.4% | 0.8% |
| After ion purification | 5~8 | 0.0% | 0.1% | 1.7% | 97.4% | 0.8% |
| After primary concentration | 23.6 | 0.0% | 0.1% | 1.7% | 97.4% | 0.8% |
| After secondary concentration | 70.3 | 0.0% | 0.1% | 2.6% | 96.3% | 1.0% |
| Final container | 70.3 | 0.0% | 0.1% | 2.6% | 96.3% | 1.0% |

As shown in the Table 3, it could be seen that the content of allulose was slightly reduced, since the intensity of steam applied in the second step was high, when concentrating to 20 to 30% by weight initially and then doing to 70 to 72% by weight again, in case of 2-step concentration of allulose using multiple effect concentration equipment.

Example 2

It was preceded by the same method as Example 1, but concentration was performed by 2-step concentration using a multiple effect evaporator in the concentration process. The concentration was performed by primary concentration from initial 5 to 15% by weight to 30 to 39% by weight, and secondary concentration to 70 to 72% by weight again.

In case of the primary concentration of allulose, the concentration was conducted, as the temperature of steam was 90° C. to 100° C., and then the temperature of the solution was increased to 50° C. to 60° C. In case of the secondary concentration, it was conducted, as the steam temperature was increased to 100° C. to 110° C. and the concentration temperature of the allulose solution was 60° C. to 70° C. The time taken in concentration of allulose fractions in multiple effect equipment was 8 minutes to 15 minutes for both the primary and secondary concentration. The concentrated product was cooled to 10 to 30° C. temperature through a heat exchanger and was packaged in a PE container. The contents by each process were shown in the following Table 4.

TABLE 4

| Classification | Brix | Saccharides including disaccharides or higher degree of polymerization | Glucose | Fructose | allulose | Reducing sugar |
|---|---|---|---|---|---|---|
| Fructose raw material | 50 | 1.1% | 4.8% | 88.3% | 0.0% | 5.8% |
| Conversion reaction product | 50 | 1.1% | 5.0% | 65.4% | 22.6% | 5.8% |
| Allulose fraction after high purity separation | 5~8 | 0.0% | 0.1% | 1.8% | 97.6% | 0.7% |
| After ion purification | 5~8 | 0.0% | 0.1% | 1.8% | 97.6% | 0.7% |
| After primary concentration | 30.8 | 0.0% | 0.1% | 1.8% | 97.6% | 0.7% |
| After secondary concentration | 70.3 | 0.0% | 0.1% | 1.8% | 97.6% | 0.7% |
| Final container | 70.3 | 0.0% | 0.1% | 1.8% | 97.6% | 0.7% |

As shown in Table 4, it could be seen that the content of allulose was stably maintained after high purity separation, when the 2-step concentration of allulose was conducted using multiple effect concentration equipment, by concentrating to initially 30 to 40% by weight and then doing to 70 to 72% by weight again.

Example 3

It was preceded by the same method as Example 1, but concentration was performed by 2-step concentration using a thin film evaporator in the concentration process.

The allulose fractions were concentrated using a centrifugal thin film evaporator after passing through an ion purification process and setting the conductivity to 20 uS/cm or less. Using the centrifugal thin film evaporator, the concentration rpm was 400 to 600 and the temperature of steam was 70° C. to 80° C., and then the temperature of the solution was increased to 40° C. to 50° C., and the primary concentration was conducted by 50 to 60% by weight from the allulose content of 5 to 15% by weight of the initial allulose solution. Consequently, in case of secondary concentration, the steam temperature was increased to 80 to 90° C., and the temperature of the solution to be concentrated was 50 to 60° C., and the secondary concentration was performed by the allulose content of 70 to 72% by weight. The time taken in concentration of allulose fractions in the centrifugal thin film vacuum concentration equipment was in a range of 30 minutes to 90 minutes for the primary concentration and secondary concentration, respectively. The concentrated solution was cooled to 10° C. to 30° C. through a heat exchanger and was packaged in a polyethylene container. The content by each process was shown in the following Table 5.

TABLE 5

| Classification | Brix | Saccharides including disaccharides or higher degree of polymerization | Glucose | Fructose | allulose | Reducing sugar |
|---|---|---|---|---|---|---|
| Fructose raw material | 50 | 1.1% | 5.0% | 88.1% | 0.0% | 5.8% |
| Conversion reaction product | 50 | 1.1% | 5.0% | 65.2% | 22.9% | 5.8% |
| Allulose fraction after high purity separation | 5~8 | 0.0% | 0.1% | 2.2% | 96.9% | 0.8% |
| After ion purification | 5~8 | 0.0% | 0.1% | 2.2% | 96.9% | 0.8% |
| After primary concentration | 54.6 | 0.0% | 0.1% | 2.2% | 96.9% | 0.8% |
| After secondary concentration | 70.5 | 0.0% | 0.1% | 2.2% | 96.9% | 0.8% |
| Final container | 70.5 | 0.0% | 0.1% | 2.2% | 96.9% | 0.8% |

As shown in Table 5, it could be seen that the content of allulose was stably maintained after high purity separation, when the 2-step concentration of allulose was conducted using centrifugal thin film vacuum concentration equipment, by concentrating to 50 to 60% by weight of the initial content and then doing to 70 to 72% by weight again.

Example 4

Using the allulose syrup obtained in Comparative example, Example 2 and Example 3, 500 g each was put in a storage container of SUS304 material, and was stored at 25° C., 35° C. and 45° C., and the allulose content change was measured once a week. The experiment was progressed for 5 weeks. The allulose contents of each week were shown in the following Table 6.

TABLE 6

| Storage period | Comparative example | | | Example 2 | | | Example 3 | | |
|---|---|---|---|---|---|---|---|---|---|
| | 25 | 35 | 45 | 25 | 35 | 45 | 25 | 35 | 45 |
| Week 0 | 95.1% | 95.1% | 95.1% | 96.3% | 96.3% | 96.3% | 97.2% | 97.2% | 97.2% |
| Week 1 | 94.9% | 94.5% | 93.6% | 96.3% | 96.3% | 95.0% | 97.2% | 97.1% | 95.8% |
| Week 2 | 94.7% | 92.9% | 91.8% | 96.1% | 96.1% | 94.2% | 97.0% | 96.8% | 94.2% |
| Week 3 | 94.4% | 92.3% | 88.5% | 96.0% | 95.9% | 92.5% | 96.8% | 96.5% | 92.4% |
| Week 4 | 94.2% | 91.9% | 86.4% | 95.9% | 95.5% | 90.5% | 96.6% | 96.2% | 90.2% |
| Week 5 | 93.9% | 91.0% | 84.6% | 95.8% | 95.2% | 88.5% | 96.5% | 95.9% | 88.4% |

As shown in the Table 6, it could be seen that the sample of Comparative example produced by 1-step concentration of allulose using the multiple effect evaporator had reduced storage stability, while products of Examples 2 and 3 had a less width of decrease than the Comparative example sample. In particular, in the 35° C. storage stability test result, the width of decrease of the content was 4.1% of Comparative example, 1.1% of Example 2, and 1.3% of Example 3, respectively, and therefore, by lowering the concentration temperature, the effect of improving the stability of allulose was obtained.

The invention claimed is:

1. A method of preparation for an allulose concentrate solution comprising
    obtaining an allulose aqueous solution having an allulose purity of 85% by weight or higher based on 100% by weight of the total solid content by performing simulated moving bed (SMB) chromatography of a conversion reaction product of allulose; and
    concentrating the allulose aqueous solution,
    wherein the concentrating is performed by two concentrating steps consecutively,
    wherein the two concentrating steps comprise a step of preparing a low concentrate solution with a total solid content of 10 Brix or more to 60 Brix or less and a step of preparing a high concentrate solution with a total solid content of more than 60 Brix to 85 Brix or less, and
    wherein the allulose concentrate solution has an allulose purity of 90% wt/wt or more, and a content of fructose and reducing sugars of 4.5% by weight or less.

2. The method of preparation according to claim 1, wherein the allulose aqueous solution comprises 90% by weight or higher of allulose based on 100% by weight of the total solid content.

3. The method of preparation according to claim 1, wherein the concentrating is performed using a thin film vacuum evaporator or a multiple effect evaporator.

4. The method of preparation according to claim 1, wherein the allulose concentrate solution has the fructose content of 3.0% by weight or less, and the content of reducing sugars of 2.5% by weight or less.

5. The method of preparation according to claim 1, wherein the allulose concentrate solution has a decreased allulose content of 3.5% by weight or less, under a storage condition at 35° C. for 5 weeks, based on 100% by weight of the allulose solid content of the allulose aqueous solution before concentration.

6. The method of preparation according to claim 1, wherein a difference between a temperature of the solution in the step of preparing the high concentrate solution and a temperature of the solution in the step of preparing the low concentrate solution is 0° C. to 35° C.

7. The method of preparation according to claim 1, wherein the concentrating is performed at a temperature condition of which a temperature of the solution in the step of preparing the high concentrate solution is 40° C. to 75° C. and a temperature of the solution in the step of preparing the low concentrate solution is 50° C. to 85° C.

8. The method of preparation according to claim 1, wherein the allulose aqueous solution has a viscosity of 2 cps to 40 cps at 45° C.

9. The method of preparation according to claim 1, wherein the allulose aqueous solution has an electrical conductivity of 0.01 to 100 uS/cm.

10. The method of preparation according to claim 1, wherein the allulose aqueous solution is an allulose fraction obtained by performing a simulated moving bed (SMB) chromatography separation process using a column chromatograph filled with cation exchange resin attached with a calcium activator.

* * * * *